US006924262B2

(12) United States Patent
Margot

(10) Patent No.: US 6,924,262 B2
(45) Date of Patent: Aug. 2, 2005

(54) USE OF UNSATURATED ESTERS AS PERFUMING INGREDIENTS

(75) Inventor: Christian Margot, Gilly (CH)

(73) Assignee: Firmenich SA, Geneva (CH)

( * ) Notice: Subject to any disclaimer, the term of this patent is extended or adjusted under 35 U.S.C. 154(b) by 360 days.

(21) Appl. No.: 09/945,029

(22) Filed: Aug. 31, 2001

(65) Prior Publication Data

US 2002/0055455 A1 May 9, 2002

(30) Foreign Application Priority Data

Sep. 14, 2000 (CH) .............................................. 1785/00

(51) Int. Cl.[7] .................................................. A61K 7/46
(52) U.S. Cl. ............................. 512/25; 512/26; 512/27; 560/190; 560/205; 560/221; 560/76; 560/95; 560/201
(58) Field of Search ............................. 512/25, 26, 27; 560/190, 205, 221, 76, 95, 201

(56) References Cited

U.S. PATENT DOCUMENTS

| | | | | |
|---|---|---|---|---|
| 4,228,265 A | | 10/1980 | Ohishi et al. | 526/230 |
| 4,510,319 A | * | 4/1985 | Willis et al. | 560/256 |
| 5,668,102 A | * | 9/1997 | Severns et al. | 510/504 |

OTHER PUBLICATIONS

N. Nazarov et al., "Rearrangement of the Allylic System: Action of hydrogen chloride on methyl propyl vinyl carbinol and 3–mthyl–3–propyl allyl alcohol and isomeriation of the corresponding chlorides in exchange reactions", Chemical Abstracts, vol. 43, No. 10—Organic Chemistry, col. 114–115 (1949).

Abstract: Yasumasa Kuwahara et al., Pherome study on acarid mites. Part IX. Syntheses of alarm pheromone analogs of the mold mite, Tyrophagus putrescentiae, and their biological activities, Agric. Biol. Chem. vol. 46 No. 7, pp. 1855–1860.

XP–002259231: Database accession no. 43:579, Database Caplus 'Online!, Chemical Abstracts Service, Columbus, Ohio (1949).

* cited by examiner

*Primary Examiner*—Monique T. Cole
(74) *Attorney, Agent, or Firm*—Winston & Strawn LLP

(57) ABSTRACT

The compound of formula (I)

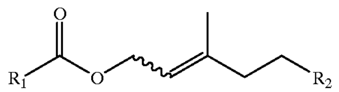

in which the wavy line represents a bond having a configuration of the type (Z) or (E), or a mixture of the two configurations; $R_1$ represents a hydrogen atom, a $C_1$ to $C_4$ linear or branched alkyl radical, a methoxy or ethoxycarbonyl radical, or an aryl radical, and $R_2$ represents a methyl or ethyl group, possess interesting organoleptic properties and can be advantageously used for the preparation of perfuming compositions to which it gives, in particular, a very natural connotation of the pear type.

10 Claims, No Drawings

USE OF UNSATURATED ESTERS AS PERFUMING INGREDIENTS

BRIEF SUMMARY OF THE INVENTION

The present invention relates to the field of perfumery. It concerns more particularly the use as perfuming ingredient of a compound of formula (I)

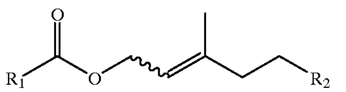

in which the wavy line represents a bond having a configuration of the type (Z) or (E), or a mixture of the two configurations; $R_1$ represents a hydrogen atom, a $C_1$ to $C_4$ linear or branched alkyl radical, a methoxy or ethoxycarbonyl radical, or an aryl radical, and $R_2$ represents a methyl or ethyl group.

The unsaturated esters of formula (I) possess very useful and appreciated odorant properties. They can be used for the preparation of perfumes, perfuming compositions and perfumed articles. They are employed to confer green and fruity type odorant notes.

BACKGROUND OF THE INVENTION

Among the compounds of formula (I), both the 3-methyl-2-hexenyl acetate and the 3-methyl-2-heptenyl formate possess a known structure. In particular, the preparation of 3-methyl-2-hexenyl acetate is described by Nasarow et al., in Zh. Obshch. Khim, 18, 1948, 656,661,663, whereas, the preparation of the 3-methyl-2-heptenyl formate is described by Y. Kuwahara in Agric. Biol. Chem. (1982), 46(7), 1855–60. On the other hand, none of the prior art documents mentions either the organoleptic properties of the compounds of formula (I), or any use of said compounds in the field of perfumery.

This is all the more surprising when knowing that some linear esters which possess a chemical structure relatively close to that of the compounds of formula (I) are well-known odorant compounds. One can cite in particular 2-hexenyl butanoate, 2-hexenyl phenyl acetate, 2-hexenyl propanoate or yet 2-hexenyl acetate. Though these compounds are listed in reference texts such as S. Arctander, Perfume and Flavor Chemicals, 1969, Montclair, N.J., USA, none of the substituted derivatives of formula (I) has been described as having odorant properties.

DETAILED DESCRIPTION OF THE INVENTION

Surprisingly, we have now been able to establish that the compounds of formula (I) possess specific and distinct odorant properties, which have been found to be particularly interesting. Indeed, these compounds, in addition to their basic green and fruity odor character, possess very original undernotes which differentiate them completely from the prior art esters of similar structure, and therefore add new nuances to the perfumer's palette.

The object of present invention is therefore the use as perfuming ingredient of a compound of formula (I)

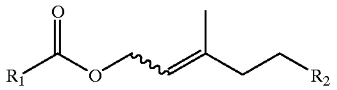

in which the wavy line represents a bond having a configuration of the type (Z) or (E), or a mixture of the two configurations; $R_1$ represents a hydrogen atom, a $C_1$ to $C_4$ linear or branched alkyl radical, a methoxy or ethoxycarbonyl radical, or an aryl radical, and $R_2$ represents a methyl or ethyl group.

Among the compounds of the invention, the compound of formula (I) wherein $R_1$ and $R_2$ represent each a methyl group, namely 3-methyl-2-hexenyl acetate, is a preferred compound according to the invention. While its structure is close to that of 3-methyl-2-hexenoic acid, known to possess a very strong perspiration odor, 3-methyl-2-hexenyl acetate possesses an odor having a particularly natural green-fruity, pear connotation. By comparison with the corresponding non-substituted ester, namely 2-hexenyl acetate, the fragrance of the compound of the invention possesses some very original undernotes of the cinnamon and bitter almond type and which give a new dimension to its fragrance, providing the perfumers with an access to new olfactive variations. This compound, which is distinct from the compounds of the prior art, is thus particularly appreciated.

Moreover, we also noticed some odor differences between the two isomers of this compound, despite their common green connotation. The perfumers showed a preference for (E)-3-methyl-2-hexenyl acetate, which possesses a more marked pear note.

Other preferred compounds of the invention are 3-methyl-2-heptenyl acetate, 3-methyl-2-hexenyl propanoate, 1-ethyl 2-(3-methyl-2-hexenyl) oxalate, 3-methyl-2-hexenyl benzoate and 3-methyl-2-hexenyl salicylate. These compounds may present themselves in the form of a mixture of isomers of configuration (Z)/(E), or in the form of either of the isomers.

The 3-methyl-2-heptenyl acetate has an odor which is more pear and less green than that of 3-methyl-2-hexenyl acetate, whereas 3-methyl-2-hexenyl propanoate has a more pronounced green character than 3-methyl-2-hexenyl acetate, whose fruity-pear note is more marked.

The salicylate and the benzoic esters of the 3-methyl-2-hexen-1-ol, namely 3-methyl-2-hexenyl benzoate and 3-methyl-2-hexenyl salicylate, are particularly remarkable for the tenacity of their green note. 3-Methyl-2-hexenyl benzoate has a very persistent green note associated with bitter almond, hyacinth, rosy notes. Finally, 3-methyl-2-hexenyl salicylate has a very natural and fresh green, foliage, pear Williams odor, which is extremely substantive on fabric. This unusual substantivity of the 3-methyl-2-hexenyl salicylate odor is a quite rare property in this type of compounds.

The compounds of the invention are suitable for use in fine perfumery, in perfumes, colognes or after-shave lotions, as well as in other current uses in perfumery such as to perfume soaps, preparations for the shower or the bath, such as bath salts, mousses, oils, gels or other preparations, products such as body oils, body-care products, body deodorants and antiperspirants, hair care products such as shampoos, ambient air deodorants, or cosmetic preparations.

The compounds of formula (I) can also be used in applications such as liquid or solid detergents for textile treatment, fabric softeners, or also in detergent compositions or cleaning products for cleaning dishes or varied surfaces, for industrial or household use.

In these applications, the compounds according to the invention can be used alone or mixed with other perfuming ingredients, solvents or additives commonly used in perfumery. The nature and variety of these co-ingredients do not require a more detailed description here, which would not be exhaustive anyway. A person skilled in the art is able to choose them by virtue of its general knowledge and according to the nature of the product that has to be perfumed and the olfactory effect sought.

These perfuming co-ingredients belong to varied chemical groups such as alcohols, aldehydes, ketones, esters, ethers, acetates, nitrites, terpenic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., USA, or more recent versions thereof, or in other similar books.

The proportions in which the compounds according to the invention can be incorporated in the different products mentioned above vary in a broad range of values. These values depend on the nature of the product that has to be perfumed and on the olfactory effect sought, as well as on the nature of the co-ingredients in a given composition when the compounds of the invention are used in admixture with perfuming co-ingredients, solvents or additives commonly used in the art.

As examples, one can cite typical concentrations from 1 to 10% by weight, even 20% or more by weight, of compound of formula (I) of the invention, with respect to the weight of the perfuming composition in which it is incorporated. Much lower concentrations than these can be used when these compounds are directly applied for perfuming some of the consumer products mentioned above.

The compounds of formula (I) are obtained by a three step synthesis. In a first step, by means of a Wittig-Horner type reaction, the hexan-2-one, respectively the pentan-2-one, are converted, in the presence of triethylphosphonoacetate, into the corresponding $\alpha,\beta$-unsaturated esters. The latter are reduced in a second step. Finally the obtained alcohols are esterified using the acyl chloride or the anhydride needed to obtain the desired compound of formula (I). The exact conditions of these reactions will be illustrated in a detailed manner in examples 1 and 2.

The invention will now be described in further detail by way of the following examples, wherein the temperatures are indicated in degrees centigrade (° C.) and the abbreviations have the usual meaning in the art.

EMBODIMENTS OF THE INVENTION

EXAMPLE 1

Preparation of Various Esters of 3-methyl-2-hexen-1-ol i) Preparation of 3-methyl-2-hepten-1-ol and 3-methyl-2-hexen-1-ol The 3-methyl-2-hepten-1-ol has been obtained according to the method described by Kuwahara, Y. et al in. J. Agric. Biol. Chem. 1982, 46, 1855, and the two isomers Z or E are also described by Nowotny, S., et al in J. Org. Chem. 1995, 60, 2762 and by Hu, T et al. in. J. Org. Chem. 1998, 63, 2401, respectively.

The 3-methyl-2-hexen-1-ol has been obtained according to an analogous process:

a) Ethyl 3-methyl-2-hexenoate

A 3 l reactor, under nitrogen atmosphere, equipped with a mechanical stirrer, was charged with 1 l of pentane, 176 g (2,1 mol) of pentan-2-one (origin: Fluka) and 470 g (2,1 mol) of triethylphosphonoacetate (origin: Fluka). Under a vigorous stirring, 780 ml (2,1 mol) of an 21% sodium ethoxyde solution in ethanol have been added dropwise over 1 h, keeping the reaction medium temperature at around 25° C. Following the reaction by gas-liquid chromatography (15 m SP-2100, 70°, 10°/min up to 220°) showed that the reaction is finished shortly after the end of the addition. Then the reaction medium was poured onto 2 l of ice cold water and vigorously stirred. The organic and aqueous phases were separated and the aqueous one washed with 100 ml of pentane. Finally, all the organic phases were combined, washed with brine, and the solvent evaporated by means of a distillation, to yield a crude product. This crude product was purified by a distillation under reduced pressure using a 15 cm Vigreux column to yield 310 g of a colorless liquid corresponding to a mixture of isomers ZiE 15:85, (yield=95%, purity=99%).

Analytical data: B.P.: 69–72° (7 mmHg)

Ethyl (Z) 3-methyl-2-hexenoate

SM: 156(38%, $M^+$); 141 (12%); 128(12%); 113 (50%); 111 (100%); 110 (10%); 100 (24%); 95 (41%); 83 (18%); 82 (39%); 81 (18%); 69 (52%); 67 (26%)

IR: 3050(w); 2960(s); 1717(s); 1649 (s); 1460(m); 1370 (m); 1219 (s); 1150 (s); 1106 (s); 1040 (s)

RMN-$^1$H: 5.66 (s, 1H); 4.13 (q, J=7.5, 2H); 2.59 (t, J=8.0, 2H); 1.87 (d, J=0.5, 3H); 1.5 (m, 2H); 1.27 (t, J=7, 3H); 0.95 (t, J=7.5, 3H)

Ethyl (E) 3-methyl-2-hexenoate

SM: 156 (24%, $M^+$); 141 (6%); 128 (26%); 113 (35%); 112 (11%); 111 (100%); 100 (28%); 95 (28%); 85 (13%); 83 (16%); 82 (43%); 69 (51%); 67 (20%)

IR: 3050 (w); 2960 (s); 1717 (s); 1649 (s); 1460 (m); 1370 (m); 1219 (s); 1150 (s); 1106 (s); 1040 (s)

RMN-$^1$H: 5.64 (s, 1H); 4.15 (q, J=7.1, 2H); 2.16 (s, 3H); 2.11 (t, J=7.6, 2H); 1.5 (m, 2H); 1.28 (t, J=7.0, 3H); 0.91 (t, J=7.3, 3H)

b) 3-Methyl-2-hexen-1-ol

A 3 l reactor, under nitrogen atmosphere, equipped with a mechanical stirrer, was charged with 0,50 l of anhydrous tetrahydrofuran (THF) and 250 ml (0,88 mol) of vitride 70% in toluene (origin: Acros, USA). The stirred mixture was cooled at 15° C., then 125 g (0,80 mol) of ethyl 3-methyl-2-hexenoate (obtained in a)) were added dropwise over 3 h. The reaction medium temperature was thus maintained at 15° C. for 1 to 2 h, time which corresponds to the end of the reaction as showed by a gas-liquid chromatography (15 m SP-2100, 70°, 10°/min up to 220°). While the reaction temperature was maintained at 15° C., 130–140 ml of a 20% NaOH solution was slowly added until formation of a viscous precipitate. The reaction mixture was filtered over celite, the filtrate decanted and the aqueous phase extracted twice with 100 ml of diethyl ether. Finally, all the organic phase were combined, washed twice with 500 ml of water, dried over sodium sulfate and the solvent evaporated by means of a distillation, to yield a crude product. A flash distillation of the crude product over a Vigreux column yielded 70 g of a clear product having a boiling point of 70°/1 mmHg.

This product contains 98% of a 22:78 mixture of isomers Z and E of 3-methyl-2-hexen-1-ol (yield=75%).

Analytical data:

(Z) 3-Methyl-2-hexen-1-ol

SM: 114 (2,5%, $M^+$); 96 (10%); 81 (17%); 71 (100%); 57 (17%)

IR: 3300 (m, large); 2956 (s); 1667 (w); 1455 (m); 1378 (m); 1064 (m); 991 (s)

RMN-$^1$H: 5.42 (t, J=6.5, 1H); 4.12 (d, J=6.5, 2H); 2.05 (t, J=8, 2H); 1.8 (s large, 1H); 1.72 (d, J=1, 3H); 1,4 (m, 2H); 0.89 (t, J=7.5, 3H)

(E) 3-Methyl-2-hexen-1-ol

SM: 114 (5%, $M^+$); 81 (11%); 71 (100%); 57 (17%)

IR: 3311 (m, large); 2956 (s); 1667 (w); 1455 (m); 1379 (m); 1065 (m); 992 (s)

RMN-$^1$H: 5.41 (t with a fine structure, J=6.5, 1H); 4.15 (d, J=6.5, 2H); 1.99 (t, J=7.5, 2H); 1.66 (s, 3H); 1.43 (hex, J=7.5, 2H); 1.2 (s large, 1H); 0.89 (t, J=7.5, 3H)

ii) General Procedure for the Esterification of the Alcohols

The esters of the invention can be prepared from the corresponding alcohol and the corresponding acyl chloride or anhydride according to one of the herein above procedure.

a) Acetic Anhydride Based Acetylation

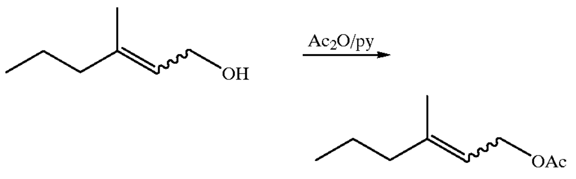

A reaction vessel is filled with 120 g (1.05 mol) of Z/E 3-methyl-2-hexen-1-ol, 500 ml pyridine and 160 ml (1.6 mol) of acetic anhydride and the mixture is stirred 1 h. During this time, the reaction temperature is kept below 30° C. with the help of an ice-water cooling bath. The mixture is poured onto 1 l of water and partitioned with 3×250 ml diethyl ether. The combined organic phases are washed with brine until neutral, dried over anhydrous sodium sulfate and concentrated by distillation of the solvents. Fractionation through a 20 cm Vigreux column yields 129 g of a colorless liquid, b.p. 72° C./1 mmHg. This liquid is a 21:79 Z/E mixture of 3-methyl-2-hexenyl acetate, purity >98% (GLC, 15 m SP-2100, 70° C., 10° C./min to 220° C.). Yield 79%.

The Z and E isomers can be separated by fractional distillation through a Fisher column. The lower boiling, minor Z isomer distills at 39–41°/13 mmHg. Once all the Z isomer has been distilled off, the remaining E isomer can be isolated from the residue through Kugelrohr distillation (Oven Temperature 70° C., 10 mmHg).

b) Process with Acetyl Chloride

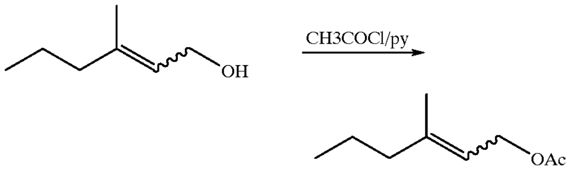

A reaction vessel, under nitrogen atmosphere, is filled with 3.0 g (26 mmol) of Z/E 3-Methyl-2-hexen-1-ol, 7.0 ml of pyridine and 3.0 g (39 mmol) of acetyl chloride and the contents are stirred 30 min. During this time, the reaction temperature is kept below 30° C. with the help of an ice-water cooling bath. The mixture is poured onto 100 ml water and partitioned with 3×50 ml pentane. The combined organic phases are washed with brine until neutral, dried over anhydrous sodium sulfate and concentrated by distillation of the solvents. Kugelrohr distillation of the concentrate produces 3.6 g colorless liquid (oven temperature 70° C., 10 mmHg), yield 90%. This material is a 1:4 Z/E mixture of 3-methyl-2-hexenyl acetate, purity 95%. It is purified by silica gel chromatography (100 g SiO2, 95:5 cyclohexane/methyl acetate elution) to afford 2.8 g pure 25:75 Z/E ester.

3-Methyl-2-hexen-1-ol and 3-methyl-2-hepten-1-ol were obtained as ca 1:4 Z/E mixtures. The esterification reactions described above produced esters with similar E/Z isomer ratios. However isolation and purification of the product by column chromatography did sometimes produce fractions with different Z/E ratios. This is why the mixtures described below have sometimes different ratios.

Products and Characterizations (Z) 3-Methyl-2-hexenyl Acetate starting materials: (Z) 3-Methyl-2-hexen-1-ol and acetic anhydride Odor: green, aldehydic green almond. At the bottom note green and fenugreek SM: 156 (0.2%, $M^+$); 97 (12%); 96 (42%); 81 (100%); 79 (12%); 71 (42%); 69 (18%); 68 (29%); 67 (21%)

IR: 2960 (m); 1736 (s); 1668 (w); 1448 (m); 1377 (m); 1224 (s); 1019 (s); 952 (m)

RMN-$^1$H: 5.36 (t, J=7.2, 1H); 4.57 (d, J=7.5, 2H); 2.08 (t, J=7.1, 2H); 2.05 (s, 3H); 1.75 (s, 3H); 1.43 (hexuplet, J=7.5, 2H); 0.90 (t, J=7.5, 3H)

RMN-$^{13}$C: 171.1 (s); 142.8 (s); 119.2 (d); 61.1 (t); 34.1 (t); 23.4 (q); 21.3 (t); 21.0 (q); 13.8 (q)

(E) 3-Methyl-2-hexenyl Acetate starting materials: (E) 3-Methyl-2-hexen-1-ol and acetic anhydride Odor: green, pear SM: 156 (0,3%, $M^+$); 97 (13%); 96 (44%); 81 (100%); 79 (12%); 71 (43%); 69 (19%); 68 (34%); 67 (24%)

IR: 2960 (m); 1736 (s); 1669 (w); 1454 (m); 1366 (m); 1226 (s); 1020 (s); 953 (m)

RMN-$^1$H: 5.33 (tq, J=7+1, 1H); 4.59 (d, J=7.1, 2H); 2.05 (s, 3H); 2.01 (t, J=7.5, 2H); 1.68 (s, 3H); 1.45 (hex, J=7.1, 2H); 0.89 (t, J=7.5, 3H)

RMN-$^{13}$C: 171.1 (s); 142.4 (s); 118.3 (d); 61.4 (t); 41.7 (t); 21.1 (q); 20.7 (t); 16.3 (q); 13.7 (q)

Z/E 3-Methyl-2-hexenyl Propionate, Mixture Z/E 1:4 starting materials: Z/E 3-methyl-2-hexen-1-ol and propionyl chloride

Odor: green, pear, nearly cinnamic, liquory

MS: minor isomer (Z): 170 (1%, M+); 97 (17%); 96 (45%); 81 (93%); 68 (28%); 57 (100%).

major isomer (E): 170 (1%, M+); 97 (21%); 96 (51%); 81 (91%); 68 (32%); 57 (100%).

IR: 3050 (w); 2956 (m); 1737 (s); 1669 (w); 1457 (m); 1365 (m); 1226 (s); 1021 (s).

RMN-$^1$H: 5.37 (t, J=6.8, 1H, minor isomer); 5.33 (tq, J=6.8+1.2, 1H, major isomer); 4.60 (d, J=7.1, 2H, major isomer); 4.57 (d, J=7, 1H, minor isomer); 2.3 (m, 2H); 2.08 (t, J=7.5, 2H, minor isomer); 2.01 (t, J=7.5, 2H. major isomer); 1.75 (s, 3H, minor isomer); 1.69 (s, 3H, major isomer); 1.5 (m, 2H); 1.14 (t, J=7.5, 3H); 0.90 (t, J=7.5, 3H, minor isomer); 0.88 (t, J=7.5, 3H, major isomer).

RMN-$^{13}$C: 174.5 (s); 142.7 (s); 142.2 (s); 119.2 (d); 118.5 (d); 61.3 (t); 61.0 (t); 41.7 (t); 34.0 (t); 27.7 (t); 23.5 (q); 21.3 (t); 20.7 (t); 16.3 (q); 13.9 (q); 13.7 (q); 9.2 (q).

3-Methyl-2-hexenyl Z/E Benzoate, Mixture Z/E 3:7 starting materials: Z/E 3-methyl-2-hexen-1-ol and benzoyl chloride

Odor: green, almond, hyacinth, rosy

MS: minor isomer (Z): 218 (2%, M+); 105 (100%); 97 (10%); 96 (55%); 81 (59%); 77 (32%).

major isomer (E): 218 (2%, m+); 105 (100%); 97 (10%); 96 (58%); 81 (57%); 77 (34%).

IR: 3080 (w); 2957 (m); 1713 (s); 1673 (w); 1600 (m); 1450 (m); 1264 (s)1096 (s); 1068 (s); 1025 (s).

RMN-$^1$H: 8.06 (d, J=8, 2H); 7.5 (m, 3H); 5.5 (m, 1H); 4.84 (d, J=7.5, 2H, major isomer); 4.82 (d, J=7, 2H, minor isomer); 2.13 (t, J=7, 2H, minor isomer); 2.02 (t, J=7, 2H, major isomer); 1.78 (d, J=0.3, 3H, minor isomer); 1.74 (s, 3H, major isomer); 1.5 (m, 2H); 0.91 (t, J=7, 3H, minor isomer); 0.89 (t, J=7, 3H, major isomer).

RMN-$^{13}$C: 166.7 (s); 142.8 (s); 142.5 (s); 132.8 (d); 130.6 (s); 129.6 (d); 128.3 (d); 119.2 (d); 118.4 (d); 61.9 (t); 61.6 (t); 41.7 (t); 34.1 (t); 23.5 (q); 21.3 (t); 20.7 (t); 16.4 (q); 13.9 (q); 13.7 (q).

Z/E 1-Ethyl 2-(3-methyl-2-hexenyl)Oxalate, Mixture Z/E 1:4 starting materials: Z/E 3-methyl-2-hexen-1-ol and ethyl oxalyl chloride

Odor: green, fruity

MS: minor isomer (Z): 113 (M-101, $C_7H_{13}O^+$, 11%); 97 (36%); 96 (19%); 81 (12%); 55 (100%).

major isomer (E): 113 (M-101, $C_7H_{13}O^+$, 12%); 97 (37%); 96 (16%); 81 (10%); 55 (100%).

IR: 2960 (m); 1765 (s); 1739 (s); 1615 (w); 1446 (m); 1380 (m); 1302 (s); 1150 (s, doublet); 1016 (m).

RMN-$^1$H: 5.43 (t, J=8, 1H, minor isomer); 5.40 (t with fine structure, J=7.5, 1H, major isomer); 4.81 (d, J=7.5, 2H, major isomer); 4.78 (d, J=7, 2H, minor isomer); 4.35 (q, J=7.2, 2H); 2.11 (t, J=7.5, 2H, minor isomer); 2.02 (d, J=7.5, 2H, major isomer); 1.77 (s, 3H, minor isomer); 1.73 (s, 3H, major isomer); 1.5 (m, 2H); 1.38 (t, J=7.2, 3H); 0.90 (t, J=7.5, 3H, minor isomer); 0.88 (t, J=7.5, 3H, major isomer).

RMN-$^{13}$C: 158.0 (s); 144.5 (s); 117.6 (d); 116.8 (a); 63.8 (t); 63.5 (t); 63.1 (t); 41.7 (t); 34.1 (t); 23.5 (q); 21.2 (t); 20.6 (t); 16.4 (q); 14.0 (q); 13.9(q); 13.7 (q).

EXAMPLE 2

Preparation of 3-methyl-2-heptenyl Acetate

This compound has been obtained by reacting the 3-methyl-2-hepten-1-ol and the acetyl chloride following the experimental procedure described in Example 1 ii) b).

Z/E 3-Methyl-2-heptenyl acetate, mixture Z/E 1:4 starting materials: Z/E 3-methyl-2-hepten-1-ol and the acetyl chloride

Odor: green, unripe pear

MS: minor isomer (Z): 170 (1%, M+); 110 (39%); 95 (35%); 81 (44%); 71 (36%); 68 (85%); 55 (35%); 43 (100%).

major isomer (E): 170 (1%, M+); 110 (39%); 95 (31%); 81 (41%); 71 (38%); 68 (90%); 55 (36%); 43 (100%).

IR: 2960 (m); 1735 (s); 1669 (w); 1457 (m); 1366 (m); 1226 (s); 1020 (s).

RMN-$^1$H: 5.33 (t, J=6, 1H); 4.59 (d, J=7.1, 2H, major isomer); 4.57 (d, J=7, 1H, minor isomer); 2.09 (t, J=7.5, 2H, minor isomer); 2.03 (t, J=7.5, 2H, major isomer); 2.05 (s, 3H); 1.75 (d, J=0.3; 3H, minor isomer); 1.69 (s; 3H, major isomer); 1.3 (m, 4H); 0.91 (t, J=7.1, 3H, minor isomer); 0.90 (t, J=7.2, 3H, major isomer).

RMN-$^{13}$C: 171.1 (s); 143.2 (s); 142.7 (s); 118.8 (d); 118.1 (d); 61.5 (t); 61.1 (t); 39.3 (t); 31.9 (t); 30.4 (t); 29.8 (t); 23.5 (q); 22.6 (t); 22.4 (t); 21.1 (q); 16.4 (q); 14.0 (q).

EXAMPLE 3

Preparation of Z/E 3-methyl-2-hexenyl Salicylate

In a Schlenk tube, under nitrogen atmosphere, 5.0 g of Z/E 3-methyl-2-hexene-1-ol (44 mmol) were dissolved in 50 ml of anhydrous THF. At −20° C., 27.5 ml of butyllithium 1.6M in hexane (44 mmol) were added dropwise over 10 minutes. The reaction mixture was allowed to warm at room temperature and then was added, over 10 minutes, a solution of 9.4 g (44 mmol) of phenyl salicylate in 50 ml of anhydrous THF. After 15 hours, the reaction mixture is poured onto 500 ml of ice cold water and partitioned with 3×50 ml diethyl ether. The combined organic phases are washed with 200 ml of cold water, dried over anhydrous sodium sulfate and concentrated by distillation of the solvents. The crude product thus obtained is purified by silica gel chromatography (200 g SiO2, 95:5 hexane/ethyl acetate elution) to afford 2.8 g pure 25:75 Z/E ester.

1.2 g of pure 1:2 Z/E mixture of 3-methyl-2-hexenyl Salicylate, purity 96%, and 1.3 g of a 90% purity fraction were obtained (yield 34%)

Odor: green, foliage, pear Williams

MS: minor isomer (Z): 138 ($C_7H_6O_3^+$, 49%); 121 (30%); 120 (50%); 97 (36%); 96 (69%); 81 (46%); 55 (100%).

major isomer (E): 138 ($C_7H_6O_3^+$, 46%); 121 (34%); 120 (53%); 97 (38%); 96 (80%); 81 (49%); 55 (100%).

IR: 3150 (broad, w); 2957 (m); 1667 (s); 1612 (s); 1584 (m); 1484 (s); 1380 (m); 1295 (s); 1209 (s); 1155 (s); 1134 (s); 1084 (s); 1032 (m).

RMN-$^1$H: 10.84 (s, 1H); 7.84 (d, J=8, 1H); 7.43 (dd, J=2+8, 1H); 6.98 (d, J=8.5, 1H); 6.87 (t, J=8, 1H); 5.5 (m, 1H); 4.87 (d, J=7.0, 2H, major isomer); 4.83 (d, J=7, 2H, minor isomer); 2.14 (t, J=7, 2H, minor isomer); 2.03 (t, J=7, 2H, major isomer); 1.79 (s, 3H, minor isomer); 1.75 (s, 3H, major isomer); 1.5 (m, 2H); 0.92 (t, J=7, 3H, minor isomer); 0.90 (t, J=7, 3H, major isomer).

RMN-$^{13}$C: 170.2 (s); 161.7(s); 143.9(s); 143.5 (s); 135.5 (d); 130.0(d); 119.1 (d); 118.5 (d); 117.7 (d); 117.5 (d); 112.7 (s); 62.2 (t); 61.9 (t); 41.7 (t); 34.1 (t); 26.9 (t); 23.5 (q); 21.3 (t); 20.7 (t); 16.4 (q); 13.9 (q); 13.7 (q).

EXAMPLE 4

Preparation of a Perfuming Composition

We have prepared a perfuming composition for a pear type accord with the following ingredients:

| Ingredients | Parts by weight |
|---|---|
| Amyl acetate | 10 |
| Hexyl acetate | 20 |
| Citronellyl acetate | 50 |
| Geranyl acetate | 40 |
| 1-p-Menthen-8-yl acetate | 90 |
| 10% * Benzaldehyde | 30 |
| 50% * n-Decanal | 20 |
| Ambrettolide ®[1)] | 20 |
| Ethyl 2-methylpentanoate[2)] | 10 |
| Raspberry ketone | 5 |
| 10% * Ethyl caproate | 20 |
| Methyl cinnamate | 10 |
| γ-n-Decalactone | 5 |
| 50% * β-Damascone[3)] | 20 |
| Diethyl 1,4-cyclohexanedicarboxylate[4)] | 30 |
| Allyl heptanoate | 10 |
| Hexyl isobutyrate | 40 |

-continued

| Ingredients | Parts by weight |
|---|---|
| Phenoxyethyl isobutyrate | 90 |
| 10% * cis-3-hexenol isobutyrate | 20 |
| Isopentyrate[5] | 20 |
| Lilial ®[6] | 70 |
| Linalool | 80 |
| 1% * Melonal[7] | 30 |
| 10% * 6,7-Epoxy-3,7-dimethyl-1,3-octadiene[8] | 30 |
| Hedione ®[9] | 50 |
| 0.1% * (2E,6Z)-2,6-Nonadienal | 40 |
| 1% * cis-3-Hexenol | 30 |
| Amyl propionate | 5 |
| Cinnamyl propionate | 5 |
| Scentenal ®[10] | 10 |
| Undecavertol ®[11] | 10 |
| Veloutone | 20 |
| Verdox ®[12] | 40 |
| Total | 980 |

* in the dipropyleneglycol
[1]origin: Givaudan-Roure SA, Vernier, Switzerland
[2]origin: Firmenich SA, Geneva, Switzerland
[3]1-(2,2,6-trimethyl-1-cyclohexen-1-yl)-2-buten-1-one; origin: Firmenich SA, Geneva, Switzerland
[4]origin: Firmenich SA, Geneva, Switzerland
[5]1,3-dimethyl-3-butenyl isobutyrate; origin: Firmenich SA, Geneva, Switzerland
[6]3-(4-tert-butylphenyl)-2-methylpropanal; origin: Givaudan-Roure SA, Vernier, Switzerland
[7]2,6-dimethyl-5-heptanal; origin: Givaudan-Roure SA, Vernier, Switzerland
[8]origin: Firmenich SA, Geneva, Switzerland
[9]Methyl dihydrojasmonate; origin: Firmenich SA, Geneva, Switzerland
[10]8(9)-methoxy-tricyclo[5.2.1.0(2,6)]decane-3(4)-carbaldehyde; origin: Firmenich SA, Geneva, Switzerland
[11]4-methyl-3-decen-5-ol; origin: Givaudan-Roure SA, Vernier, Switzerland
[12]2-tert-butyl-1-cyclohexyl acetate; origin: International Flavors and Fragrances, USA The addition of 20 parts by weight of 3-methyl-2-hexenyl acetate to this fruity base with an apple-pear connotation provided a new composition having an odor wherein the pear note was particularly strong, while the apple note was weaker. Moreover, the compound of the invention imparted to the odor of the composition a nice, fresh, green connotation, very natural.

EXAMPLE 5

Preparation of a Perfuming Composition

We have prepared a perfuming composition of the floral-musky type with the following ingredients:

| Ingredients | Parts by weight |
|---|---|
| 10% * Amyl acetate | 20 |
| Benzyl acetate | 100 |
| Styrallyl acetate | 15 |
| Verdyl acetate | 40 |
| Allyl amyl glycolate | 5 |
| γ-Undecalactone | 15 |
| Citronellol | 80 |
| 10% * β-Damascone[1] | 20 |
| Habanolide ®[2] | 70 |
| Hedione ®[3] | 150 |
| Heliopropanal[4] | 20 |
| Heliotropine | 20 |
| Iralia ®[5] | 15 |
| Lilial ®[6] | 80 |
| Linalool | 70 |
| 1% * Cis-2-methyl-4-propyl-1,3-oxathiane[7] | 20 |

-continued

| Ingredients | Parts by weight |
|---|---|
| Cis-3-hexenol salicylate | 40 |
| Phenethylol | 100 |
| Terpineol | 80 |
| 10% * Zestover[8] | 20 |
| Total | 980 |

* in the dipropyleneglycol
[1]1-(2,6,6-trimethyl-1-cyclohexen-1-yl)-2-buten-1-one; origin: Firmenich SA, Geneva, Switzerland
[2]pentadecenolide; origin: Firmenich SA, Geneva, Switzerland
[3]methyl dihydrojasmonate; origin: Firmenich SA, Geneva, Switzerland
[4]3-(1,3-benzodioxol-5-yl)-2-methylpropanal; origin: Firmenich SA, Geneva, Switzerland
[5]mixture of methylionone isomers; origin: Firmenich SA, Geneva, Switzerland
[6]3-(4-tert-butylphenyl)-2-methylpropanal; origin: Givaudan-Roure SA, Vernier, Switzerland
[7]origin: Firmenich SA, Geneva, Switzerland
[8]2,4-dimethyl-3-cyclohexen-1-carbaldehyde; origin: Firmenich SA, Geneva, Switzerland The addition of 20 parts by weight of 3-methyl-2-hexenyl acetate to this base composition with a floral-musky character, provided a new composition with a totally original green-ethereal connotation, together with a slightly fruity, pear-quince character. Moreover, this new composition was quite different from a fragrance point of view from a similar base composition to which trans-2-hexenyl acetate would have been added.

What I claim is:

1. A method to confer, improve, enhance or modify the odor properties of a perfuming composition or a perfumed product, which method comprises the step of adding to said composition or product a compound of formula (I)

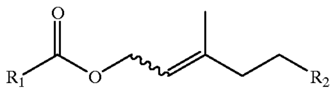

in which the wavy line represents a bond having a configuration of the type (Z) or (E), or a mixture of the two configurations; $R_1$ represents a hydrogen atom, a $C_1$ to $C_4$ linear or branched alkyl radical, a methoxy or ethoxycarbonyl radical, or an aryl radical, and $R_2$ represents a methyl or ethyl group.

2. The method according to claim 1, of 3-methyl-2-hexenyl acetate, 3-methyl-2-heptenyl acetate, 3-methyl-2-hexenyl propanoate, 1-ethyl 2-(3-methyl-2-hexenyl) oxalate or 3-methyl-2-hexenyl salicylate.

3. Perfuming composition or perfumed article, comprising as active ingredient a compound of formula (I)

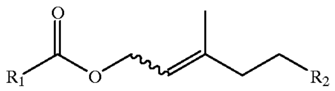

in which the wavy line represents a bond having a configuration of the type (Z) or (E), or a mixture of the two configurations; $R_1$ represents a hydrogen atom, a $C_1$ to $C_4$ linear or branched alkyl radical, a methoxy or ethoxycarbonyl radical, or an aryl radical, and $R_2$ represents a methyl or ethyl group.

4. Perfuming composition or perfumed article according to claim 3, wherein the active ingredient is 3-methyl-2-hexenyl acetate, 3-methyl-2-heptenyl acetate or 3-methyl-2-hexenyl propanoate.

5. Perfuming composition or perfumed article according to claim 3, wherein the active ingredient is 1-ethyl 2-(3-methyl-2-hexenyl) oxalate or 3-methyl-2-hexenyl salicylate.

6. Perfumed article according to claim 3, in the form of a perfume, a cologne, an after-shave lotion, a soap, preparations for the shower or the bath, a body-care product or hair-care product, a deodorant or antiperspirant or an airfreshener, a cosmetic preparation, a detergent or fabric softener or an all-purpose cleaner.

7. Compound of formula (I)

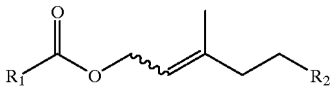

in which the wavy line represents a bond having a configuration of the type (Z) or (E), or a mixture of the two configurations; $R_1$ represents a hydrogen atom, a $C_1$ to $C_4$ linear or branched alkyl radical, a methoxy or ethoxycarbonyl radical, or an aryl radical, and $R_2$ represents a methyl or ethyl group provided that 3-methyl-2-hexenyl acetate and 3-methyl-2-heptenyl acetate or 3-methyl-2-hexenyl propanoate.

8. The compound according to claim 7, which is 3-methyl-2-hexenyl acetate or 3-methyl-2-hexenyl salicylate.

9. The method according to claim 1 wherein the compound is present in an amount sufficient to impart a green, fruity odor to the composition or product.

10. The perfuming composition or perfumed article according to claim 3 wherein the compound is present in an amount sufficient to impart a green, fruity odor to the composition or product.

* * * * *